United States Patent
Bäckström et al.

(10) Patent No.: US 6,436,902 B1
(45) Date of Patent: Aug. 20, 2002

(54) THERAPEUTIC PREPARATIONS FOR INHALATION

(75) Inventors: Kjell Bäckström, Lund (SE); Björn Wallmark, Berlin (DE); Magnus Dahlbäck, Lund (SE); Peter Edman, Kullavik (SE); Ann Johansson, Höllviken (SE)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 09/383,590

(22) Filed: Aug. 26, 1999

Related U.S. Application Data (63) Continuation of application No. 08/586,768, filed on Jan. 30, 1996, now abandoned, which is a continuation of application No. PCT/SE95/01475, filed on Dec. 8, 1995.

(30) Foreign Application Priority Data

Dec. 22, 1994 (SE) ............................................... 9404449
Jul. 12, 1995 (SE) ............................................... 9502576

(51) Int. Cl.$^7$ .......................... A61K 38/28; A61K 9/14; A61K 9/16
(52) U.S. Cl. .......................... 514/12; 514/826; 424/400; 424/499
(58) Field of Search ..................... 128/203.12, 203.15; 424/400, 499; 514/12, 826

(56) References Cited

U.S. PATENT DOCUMENTS

| | | | |
|---|---|---|---|
| 2,992,645 A | 7/1961 | Fowler ........................ 128/208 |
| 3,014,844 A | 12/1961 | Thiel et al. .................... 167/82 |
| 4,613,500 A | 9/1986 | Suzuki et al. ............... 424/85.4 |
| 4,690,952 A | 9/1987 | Kagatani et al. ............... 514/11 |
| 4,788,221 A | 11/1988 | Kagatani et al. ............... 514/12 |
| 4,847,298 A | 7/1989 | Alexander et al. ........... 514/565 |
| 4,895,719 A | 1/1990 | Radhakrishnan et al. ...... 424/45 |
| 4,900,730 A | 2/1990 | Miyauchi ..................... 514/12 |
| 4,907,583 A | 3/1990 | Wetterlin et al. ....... 128/203.15 |
| 4,963,367 A | 10/1990 | Ecanow ...................... 424/485 |
| 4,994,439 A | 2/1991 | Longenecker et al. ......... 514/3 |
| 5,006,343 A | 4/1991 | Benson et al. ............... 424/450 |
| 5,011,678 A | 4/1991 | Wang et al. ................... 424/45 |
| 5,118,494 A | 6/1992 | Schultz et al. ................. 424/45 |
| 5,122,127 A | 6/1992 | Stanley ..................... 604/890.1 |
| 5,122,376 A | 6/1992 | Aliverti et al. ............... 424/405 |
| 5,179,079 A | 1/1993 | Hansen et al. .................. 514/4 |
| 5,200,393 A | 4/1993 | Weiner ........................... 514/3 |
| 5,202,129 A | 4/1993 | Samajima et al. ........... 424/489 |
| 5,284,656 A | 2/1994 | Platz et al. ................. 424/435 |
| 5,320,094 A | 6/1994 | Laube et al. ............ 128/203.12 |
| 5,341,800 A | 8/1994 | Clark et al. ............ 128/203.15 |
| 5,348,730 A | 9/1994 | Greenleaf et al. ............ 424/45 |
| 5,349,947 A | 9/1994 | Newhouse et al. ..... 128/203.21 |
| 5,354,562 A | 10/1994 | Platz et al. ................. 424/489 |
| 5,364,838 A | 11/1994 | Rubsamen ..................... 514/3 |
| 5,384,133 A | 1/1995 | Boyes et al. ................. 424/501 |
| 5,419,315 A | 5/1995 | Rubsamen ................. 128/200 |
| 5,437,271 A | 8/1995 | Hodson et al. ......... 128/203.15 |
| 5,451,569 A | 9/1995 | Wong et al. ...................... 54/3 |
| 5,482,706 A | 1/1996 | Igari et al. ................. 424/85.7 |
| 5,506,203 A | 4/1996 | Backstrom et al. ............. 514/4 |
| 5,514,670 A | 5/1996 | Friedman et al. ............... 514/2 |
| 5,518,998 A | 5/1996 | Backstrom et al. ............. 514/3 |
| 5,607,915 A | 3/1997 | Patton .......................... 514/12 |
| 5,661,130 A | 8/1997 | Meezan et al. ................ 514/25 |
| 5,707,644 A | 1/1998 | Illum ........................... 424/434 |
| 5,730,969 A | 3/1998 | Hora et al. .................. 424/85.1 |
| 5,747,445 A | 5/1998 | Backstrom et al. ............. 514/4 |
| 5,997,848 A | 12/1999 | Patton et al. .................. 424/46 |
| 6,051,256 A | 4/2000 | Platz et al. .................. 424/489 |

FOREIGN PATENT DOCUMENTS

| | | |
|---|---|---|
| DE | 261 096 A1 | 10/1988 |
| EP | 0 023 359 | 7/1980 |
| EP | 312052 A1 | 10/1987 |
| EP | 364235 A1 | 4/1988 |
| EP | 0 360 340 | 3/1990 |
| GB | 837465 | 6/1960 |
| GB | 1242211 | 8/1971 |
| GB | 1520247 | 8/1978 |
| GB | 1569611 | 6/1980 |
| JP | 1117825 | 2/1987 |
| JP | 632932 | 7/1988 |
| JP | 4041421 | 6/1990 |
| JP | 4149126 | 5/1992 |
| WO | 88/09163 | 12/1988 |
| WO | WO 91/16038 | 10/1991 |
| WO | WO 91/16882 | 11/1991 |
| WO | WO 92/04069 | 3/1992 |
| WO | WO 92/06704 | 4/1992 |
| WO | 9407514 | 4/1994 |
| WO | WO 95/00151 | 1/1995 |
| WO | WO 97/10850 | 3/1997 |

OTHER PUBLICATIONS

Li et al., "Effect of a . . . ," Eur. J. Pharm. Biopharm., 39:216–221, 1993.

Byron et al., "Drug Delivery via the Respiratory . . . ," Journal of Aerosol Medicine, 7:49–75, 1994.

Nagano et al., "New Method of Insulin . . . ," Jikeikai Med. J., 32:503–506, 1985.

Elliott et al., "Parenteral absorption of insulin . . . ," Aust. Paediatr. J., 23:293–297, 1987.

(List continued on next page.)

*Primary Examiner*—Michael Borin
(74) *Attorney, Agent, or Firm*—Fish & Richardson P.C.

(57) ABSTRACT

The present invention relates to compositions and methods for pulmonary administration of full-length parathyroid hormone to mammalian hosts for the treatment of osteoporosis. Thus there is provided a therapeutic preparation comprising a human full-length parathyroid hormone, or homologues thereof, in the form of a dry powder suitable for inhalation in which at least 50% of said dry powder consists of (a) particles having a diameter of up to 10 microns; or (b) agglomerates of such particles.

68 Claims, 1 Drawing Sheet

OTHER PUBLICATIONS

Sakr., "A new approach for insulin . . . ," International Journal of Pharmaceutics, 86:1–7, 1992.

Liu et al., "Pulmonary Delivery of Free . . . ," Pharmaceutical Research, 10:228–232, 1993.

Jaegfeldt et al., "Particle size distribution from different modifications . . . ," Proceedings of an international workshop on a new inhaler, May 21–22, 1987, London, U.K., pp. 90–99.

Li et al., "Effect of a Conjugated Bile Salt on the Pulmonary . . . ," Eur. J. Pharm. Biopharm, vol. 39, pp. 216–221, 1993.

Okumura et al., "Intratracheal delivery of insulin Absorption . . . ," International Journal of Pharmaceutics, vol. 88, pp. 63–73, 1992.

Wetterlin, "Turbuhaler: A New Powder Inhaler for Administration . . . ," Pharmaceutical Research, vol. 5, pp. 506–508, 1988.

Yamamoto et al., "Absorption Enhancement of Intrapulmonary Administered Insulin . . . ," J. Pharm. Pharmacol, vol. 46, pp. 14–18, 1994.

"Bioavailability of pulmonary delivered peptides and proteins: alpha–interferon, calcitonins and parathyroid hormones", J. Control. Release (Netherlands), (1994), 28/1–3, pp. 79–85.

Almer et al., *Diabetes Res. and Clin. Pract*, 5:S163 (1988).

Bjork, Acta Univ. Uppsala, Comprehensive Summaries of Uppsala Dissertations from the Faculty of Pharmacy, 103 (1993).

Laube et al., "Preliminary Study of the Efficacy of Insulin Aerosol Delivered by Oral Inhalation in Diabetic Patients", *JAMA*, 269(16):2106–2109 (1993).

Lee et al., "Intranasal Bioavailability of Insulin Powder Formulations: Effect of Permeation Enhancer–to–Protein Ratio", *J. Pharm. Sci.*, 80(8):725–729, (1991).

Lee et al., "Mucosal Penetration Enhancers for Facilitation of Peptide and Protein Drug Absorption", *Critical Rev. Therapeut. Drug Carrier Systems*, 8(2):91–192 (1991).

Komada et al., "Intratracheal Delivery of Peptide and Protein Agents: Absorption from Solution and Dry Powder by Rat Lung", *J. Pharm. Sciences*, 83(6):863–867 (1994).

Ruin, Sydsvenska (Dagbladet), Monday, Jun. 12, 1989, Diabetics May Not Need their Insulin Shots.

Schipper et al., "Nasal Insulin Delivery with Dimethyl–β–Cyclodextrin as an Absorpotion Enhancer in Rabbits: Powder More Effective than Liquid Formulations", *Pharm. Res.*, 10(5):682–686 (1993).

Timisina et al., "Drug delivery to the respiratory tract using dry powder inhalers", *International Journal of Pharmaceutics*, 101:1–13 (1994).

Wearley, "Recent Progress in Protein and Peptide Delivery by Noninvasive Routes", *Crit. Rev. Therapeutic Drug Carrier Systems*, 8(4):331–394 (1991).

Gordon et al., Nasal Absorption of Insulin: Enhancement by Hydrophobic Bile Salts; Proc. Natl. Acad. Sci. 82:7419–7423, 1985.

Zinman, The Physiologic Replacement of Insulin, The New England Journal of Medicine 321/6:363–370, 1989.

Olanoff et al., Method to Enhance Intranasal Peptide Delivery, *Controlled–Release Technology Pharmaceutical Applications*, Lee et al., Ed. Published 1987 by the American Chemical Society, pp. 301–309.

Mishima et al., Studies on the Promoting Effects of Medium Chain Fatty Acid Salts on the Nasal Absorption of Insulin in Rats, J. Pharm. Sci. 10:624–631, 1987.

THERAPEUTIC PREPARATIONS FOR INHALATION

This application is a continuation of U.S. Ser. No. 08/586,768, filed Jan. 30, 1996, now abandoned, which is a continuation of PCT/SE95/01475, filed Dec. 8, 1995.

TECHNICAL FIELD

The present invention relates to compositions and methods for pulmonary administration of parathyroid hormone (parathormone, PTH) to mammalian hosts for the treatment of osteoporosis.

BACKGROUND ART

Human parathyroid hormone is an 84 amino acid protein (SEQ ID NO: 1) involved in calcium and phosphorus homeostasis and control of bone growth and density. Human PTH may be obtained through peptide synthesis or from genetically engineered yeast, bacterial or mammalian cell hosts. Human PTH is also commercially available from Bachem Inc., Bubendorf, Switzerland. Production of recombinant human parathyroid hormone is disclosed in EP-B0383751.

In mammals, the balance between bone formation, associated with the activity of osteoblasts, on one hand, and bone loss, associated with the activity of osteoclasts, on the other hand, is disturbed in several bone affecting diseases, such as osteoporosis. Parathyroid hormone has been shown to have a potential therapeutic role in osteoporosis. The anabolic actions of parathyroid hormone on bone are reviewed in Dempster et al. (1993) Endocrine Reviews, vol. 14, 690–709.

The N-terminal fragment of human PTH (PTH 1–34) was shown to have an anabolic effect on trabecular bone in involutional osteoporosis by Reeve et al. (1980) British Medical Journal, vol. 280, 1340–1344. However, the administration of a wild-type protein is to be preferred when possible, since this will ensure that all biological effects of the natural protein are exerted by the administered compound.

Polypeptide drugs such as PTH cannot be orally administered in effective doses, since they are rapidly degraded by enzymes in the gastrointestinal tract, and by the low pH in the stomach, before they can reach the bloodstream. Administration of PTH has generally been accomplished subcutaneously by injection. However, injection on a daily basis is inconvenient for the patient. Because of these disadvantages, there is a need for PTH in a form which is administrable other than by injection.

Pulmonary delivery of parathyroid hormone and N-terminal fragments thereof to rats is disclosed in WO 94/07514. When the N-terminal fragment consisting of amino acids 1–34 (PTH34) was administered to rats intratracheally (IT), the serum profile exhibited a peak after 15 minutes with activity diminishing rapidly thereafter. In contrast, the serum profile after IT administration of full-length PTH (ME84) exhibited a plateau which did not diminish significantly during the 90 minutes of the experiment. Since it is known that PTH is most effectively delivered to a patient in pulsatile fashion, i.e. serum concentrations should rise rapidly after administration and fall rapidly after a peak has been reached, it is concluded in the document WO 94/07514 that N-terminal fragments of PTH is preferred over the full-length protein for pulmonary delivery.

SUMMARY OF THE INVENTIVE CONCEPT

According to the present invention it has been shown that a pulsative plasma profile is obtained when full-length PTH as a dry powder aerosol is inhaled via an endotracheal tube by dogs. It has thus surprisingly been shown that pulmonary administration of full-length PTH, contrary to the conclusions expressed in the published patent application WO 94/07514, will be effective for stimulating bone formation and for the treatment of osteoporosis.

BRIEF DESCRIPTION OF THE DRAWING

FIG. 1 Plasma concentration in dogs after inhalation of PTH 1–34 and PTH 1–84, respectively. (-■-) PTH 1–84 (inhaled dose 14 μg/kg); (..▲..) PTH 1–34 (inhaled dose 4.0 μg/kg).

DISCLOSURE OF THE INVENTION

In a first aspect of the invention there is provided a therapeutic material, which preferably is a therapeutic preparation, comprising a parathyroid hormone having substantially the biological activities of full-length parathyroid hormone. The said therapeutic material is in the form of a dry powder suitable for inhalation in which at least 50% of the total mass of the active compound PTH consists of (a) primary particles having a diameter of less than about 10 microns, for example between 0.01 and 10 microns, and preferably between 1 and 6 microns, or (b) agglomerates of said particles.

The therapeutic preparation of the present invention may contain only the said active compound PTH, or it may contain other substances, such as a pharmaceutically acceptable carrier. This carrier may largely consist of particles having a diameter of less than about 10 microns, so that at least 50% of the resultant powder as a whole consists of optionally agglomerated primary particles having a diameter of less than about 10 microns, for example between 0.01 and 10 microns, and preferably between 1 and 6 microns, or (b) agglomerates of said particles.

Alternatively, the carrier may largely consist of much bigger particles ("coarse particles"), so that an "ordered mixture" may be formed between the active compounds and the said carrier. In an ordered mixture, alternatively known as an interactive or adhesive mixture, fine drug particles (in this invention, the active compounds) are fairly evenly distributed over the surface of coarse excipient particles (in this invention, the pharmaceutically acceptable carrier). Preferably in such case the active compounds are not in the form of agglomerates prior to formation of the ordered mixture. The coarse particles may have a diameter of over 20 microns, such as over 60 microns. Above these lower limits; the diameter of the coarse particles is not of critical importance so various coarse particle sizes may be used, if desired according to the practical requirements of the particular formulation. There is no requirement for the coarse particles in the ordered mixture to be of the same size,.but the coarse particles may advantageously be of similar size within the ordered mixture. Preferably, the coarse particles have a diameter of 60–800 microns.

Preferably at least 60%, such as at least 70% or at least 80%, and more preferably at least 90% of the total mass of the active compound PTH consists of particles having a diameter of less than about 10 microns, or of agglomerates of such particles. When the dry powder preparation comprises carrier, other than when an ordered mixture is desired, preferably at least 60%, such as at least 70% or at least 80%, and more preferably at least 90% by mass of the total dry powder consists of particles having a diameter of less than about 10 microns, or of agglomerates of such particles.

While the dry powder for inhalation, whether with or without pharmaceutically acceptable carrier, may contain agglomerates of particles as indicated above, at the time of inhalation any agglomerates should be substantially deagglomerated yielding a powder of which at least 50% consists of particles having a diameter of up to 10 microns. The agglomerates can be the result of a controlled agglomeration process or they may simply be the result of the intimate contact of the powder particles. In either case it is essential that the agglomerates are capable of being de-agglomerated e.g. by mechanical means in the inhaler or otherwise, into the aforesaid particles. Agglomerates are in general preferably not formed in the ordered mixture. In the case of an ordered mixture, the active compounds should be released from the large particles preferably upon inhalation, either by mechanical means in the inhaler or simply by the action of inhalation, or by other means, the active compounds then being deposited in the lower respiratory tract and the carrier particles in the mouth.

When desirable, it will be possible to include in the preparation a substance which enhances the absorption of PTH in the lower respiratory tract. Such a substance can be any of a number of compounds which act to enhance absorption through the layer of epithelial cells lining the alveoli of the lungs and into the adjacent pulmonary vasculature. Examples of enhancers are salts of fatty acids, e.g. sodium caprate, bile salts and derivatives thereof; phospholipids; chelators; and cyclodextrins and derivatives thereof. Additional examples of suitable enhancers can be found in the International Patent Applications WO 95/00127 and WO 95/00128.

The parathyroid hormone to be used according to the invention is preferably a human parathyroid hormone, although any biologically active form or derivative of PTH, having substantially the biological activities of full-length parathyroid hormone, may be used.

Preferably, the PTH to be used according to the invention is a parathyroid hormone which comprises at least amino acids 1 to 34, more preferably amino acids 1 to 84, of the sequence shown as SEQ ID NO: 1 in the Sequence Listing. However, the PTH to be used according to the invention is not to be limited strictly to PTH having the sequence shown in the Sequence Listing. Rather the invention encompasses use of PTH polypeptides carrying modifications like substitutions, small deletions, insertions or inversions, which polypeptides nevertheless have substantially the biological activities of the full-length PTH which amino acid sequence is disclosed in the Sequence Listing. Included in the invention are consequently also the use of polypeptides, the amino acid sequence of which is at least 90% homologous, preferably at least 95% homologous, with the amino acid sequence shown in the Sequence Listing. Modifications of full-length PTH can be developed in order to improve various properties, for example to improve stability or give an improved pharmacokinetic profile (i.e. improved profile of absorption through the epithelial membranes).

As stated above, additive substances commonly included in therapeutic preparations, such as pharmaceutically acceptable carriers, may be included in the therapeutic preparation of the present invention. Additive substances may be included for example in order to dilute the powder to an amount which is suitable for delivery from the particular intended powder inhaler; to facilitate the processing of the preparation; to improve the powder properties of the preparation; to improve the stability of the preparation, e.g. by means of antioxidantia or pH-adjusting compounds; or to add a taste to the preparation. Any additive should not adversely affect the stability of PTH, or disadvantageously interfere with absorption of PTH. It should also be stable, not hygroscopic, have good powder properties and have no adverse effects in the airways.

As examples of potential additives may be mentioned mono-, di-, and polysaccharides, sugar alcohols and other polyols, such as for example lactose, glucose, raffinose, melezitose, lactitol, maltitol, trehalose, sucrose, mannitol and starch. Depending upon the inhaler to be used, the total amount of such additives may vary over a very wide range.

In some circumstances little or no additive would be required, whereas for example in the case of an inhaler requiring large powder volumes for operation, a very high percentage or the therapeutic preparation could consist of additive. The amount of additive desirable would be easily determined by a person skilled in the art according to particular circumstances.

A useful mechanism for delivery of the powder according to the invention into the lungs of a patient is through a portable inhaler device suitable for dry powder inhalation. Many such devices, typically designed to deliver antiasthmatic or antiinflammatory agents into the respiratory system, are on the market Preferably the device is a dry powder inhaler of a design which provides protection of the powder from moisture and has no risk for overdosing, i.e. for occasional large doses. In addition as many as possible of the following characteristics are desired: protection of the powder from light; high respirable fraction and high lung deposition in a broad flow rate interval; low deviation of dose and respirable fraction; low retention of powder in the mouthpiece; low adsorption to the inhaler surfaces; flexibility in dose size; and low inhalation resistance.

The inhaler is preferably a single dose inhaler although a multi dose inhaler, preferably such as a multi dose, breath actuated, dry powder inhaler for multiple use, may also be employed. A suitable multi dose inhaler is described in EP-B-0069715 and in EP-B0237507. Preferably the inhaler used is a unit dose, breath actuated, dry powder inhaler for single use. A preferable unit dose inhaler is described in EP-A-0548166 and in EP-A-0558879.

Consequently, a further aspect of the invention is the use of a therapeutic preparation according to the invention in an inhalation device. Preferably, the said inhalation device provides protection of the powder for inhalation from moisture, and has minimal risk of overdosing. The said inhalation device can be e.g. a unit dose, breath actuated, dry powder inhaler for single usage, or a multi dose, breath actuated, dry powder inhaler for multiple use.

Yet a further aspect of the invention is a dry powder inhalation device containing the therapeutic preparation as defined above.

A further important aspect of the invention is a process for the manufacture of a therapeutic preparation as defined above. The described powder preparation can be manufactured in several ways, using conventional techniques. It may be necessary to micronise the active compounds and if appropriate (i.e where an ordered mixture is not intended) any carrier in a suitable mill, for example in a jet mill at some point in the process, in order to produce primary particles in a size range appropriate for maximal deposition in the lower respiratory tract (i.e., under 10 $\mu$m). For example, one can dry mix PTH and carrier, where appropriate, and then micronise the substances together; alternatively, the substances can be micronised separately, and then mixed. Where the compounds to be mixed have different physical properties such as hardness and brittleness, resistance to micronisation varies and they may require different pressures to be broken down to suitable particle sizes. When micronised together, therefore, the obtained particle size of one of the components may be unsatisfactory. In such case it would be advantageous to micronise the different components separately and then mix them.

It is also possible first to dissolve the active component including, where an ordered mixture is not intended, any carrier in a suitable solvent, e.g. water, to obtain mixing on the molecular level. This procedure also makes it possible to adjust the pH-value to a desired level. The pharmaceutically accepted limits of pH 3.0 to 8.5 for inhalation products must be taken into account, since products with a pH outside these limits may induce irritation and constriction of the airways. To obtain a powder, the solvent must be removed by a process which retains the biological activity of PTH. Suitable drying methods include vacuum concentration, open drying, spray drying, freeze drying and use of supercritical fluids. Temperatures over 40° C. for more than a few minutes should generally be avoided, as some degradation of the PTH may occur. Following the drying step, the solid material can, if necessary, be ground to obtain a coarse powder, then, if necessary, micronised.

If desired, the micronised powder can be processed to improve the flow properties, e.g., by dry granulation to form spherical agglomerates with superior handling characteristics, before it is incorporated into the intended inhaler device. In such a case, the device would be configured to ensure that the agglomerates are substantially deagglomerated prior to exiting the device, so that the particles entering the respiratory tract of the patient are largely within the desired size range.

Where an ordered mixture is desired, the active compound may be processed, for example by micronisation, in order to obtain, if desired, particles within a particular size range. The carrier may also be processed, for example to obtain a desired size and desirable surface properties, such as a particular surface to weight ratio, or a certain ruggedness, and to ensure optimal adhesion forces in the ordered mixture. Such physical requirements of an ordered mixture are well known, as are the various means of obtaining an ordered mixture which fulfils the said requirements, and may be determined easily by the skilled person according to the particular circumstances.

Yet a further aspect of the invention is a method for the treatment of osteoporosis comprising administering, to a patient in need thereof, an effective amount of a therapeutic preparation as defined above. Suitable doses can be in the range of 1 to 100 μg full-length PTH/kg, e.g. around 30 μg/kg.

The invention will now be described by way of Examples, which are intended to illustrate but not limit the scope of the invention.

EXAMPLES

EXAMPLE 1

1.1. Therapeutic Preparation of PTH 1–84 for Inhalation

An aqueous solution with the following composition is made:

| | |
|---|---:|
| Human PTH 1–84 | 41 mg |
| Citric acid, monohydrate | 57 mg |
| Sodium citrate | 113 mg |
| Lactose | 3888 mg |
| Water | approx. 53 ml |

The pH is adjusted to 5.0. The solution is concentrated by evaporation, at a temperature of 37° C., over a period of about one day. The obtained solid cake is crushed and sieved through a 0.5 mm sieve, and the resultant powder micronised through a jet mill to particles of about 2 microns in diameter.

1.2. Therapeutic Preparation of PTH 1–34 for Inhalation

An aqueous solution with the following composition is made:

| | |
|---|---:|
| Human PTH 1–34 | 11.2 mg |
| Citric acid, monohydrate | 66 mg |
| Sodium citrate | 131 mg |
| Lactose | 4589 mg |
| Water | approx 52 ml |

The solution is further treated as described in Example 1.1. above.

1.3. Therapeutic PTH Preparation Including an Enhancer

An aqueous solution with the following composition is made:

| | |
|---|---:|
| Human PTH 1–84 | 50 mg |
| Citric acid, monohydrate | 69 mg |
| Sodium citrate | 138 mg |
| Sodium taurocholate | 17 mg |
| Lactose | 4726 mg |
| Water | approx. 60 ml |

The pH is adjusted to 5.0. The solution is concentrated by evaporation, at a temperature of 37° C., over a period of about one day. The obtained solid cake is crushed and sieved through a 0.5 mm sieve, and the resultant powder micronised through a jet mill to particles of about 2 microns in diameter.

EXAMPLE 2

Pharmacokinetic Studies 2.1. Powder Formulation and Inhalation System

Human PTH 1–84 or PTH 1–34 were prepared according to Examples 1.1 and 1.3, respectively. The powder formulations were compressed in dust containers and generated continuously as dry powder aerosols by a Wright Dust Feed (WDF). The aerosols were generated by scraping off the formulations from the tablets in the dust containers. The mass flow through the WDF was 8.0 l/min.

The inhaled dose (ID) was determined by measuring the inspiratory tidal volume (ITV) and the PTH concentration during inhalation.

2.2. Treatment

Beagle dogs (n=5, at each formulation) were starved for 16 hours before inhalation and the experiments were performed in the mornings. The dogs were anaesthetized with Plegecil® and Penthotal®, intubated and exposed with either PTH 1–34 or PTH 1–84 for about 10 minutes.

Venous blood samples for determination of PTH concentration were taken from the jugular vein into heparinized vacutainer tubes (2 ml). The samples were collected before dosing and at 10, 15, 20, 30, 40, 60, 90, 120, 240 and 360 minutes after start (t=0) of inhalation. The whole blood samples were centrifuged immediately, alternatively kept in ice water for maximum 20 minutes before centrifugation, and the plasma (1 ml) was sampled for PTH analysis. PTH in plasma was analyzed using radioimmunoassay (RIA) kits.

Figure 1:
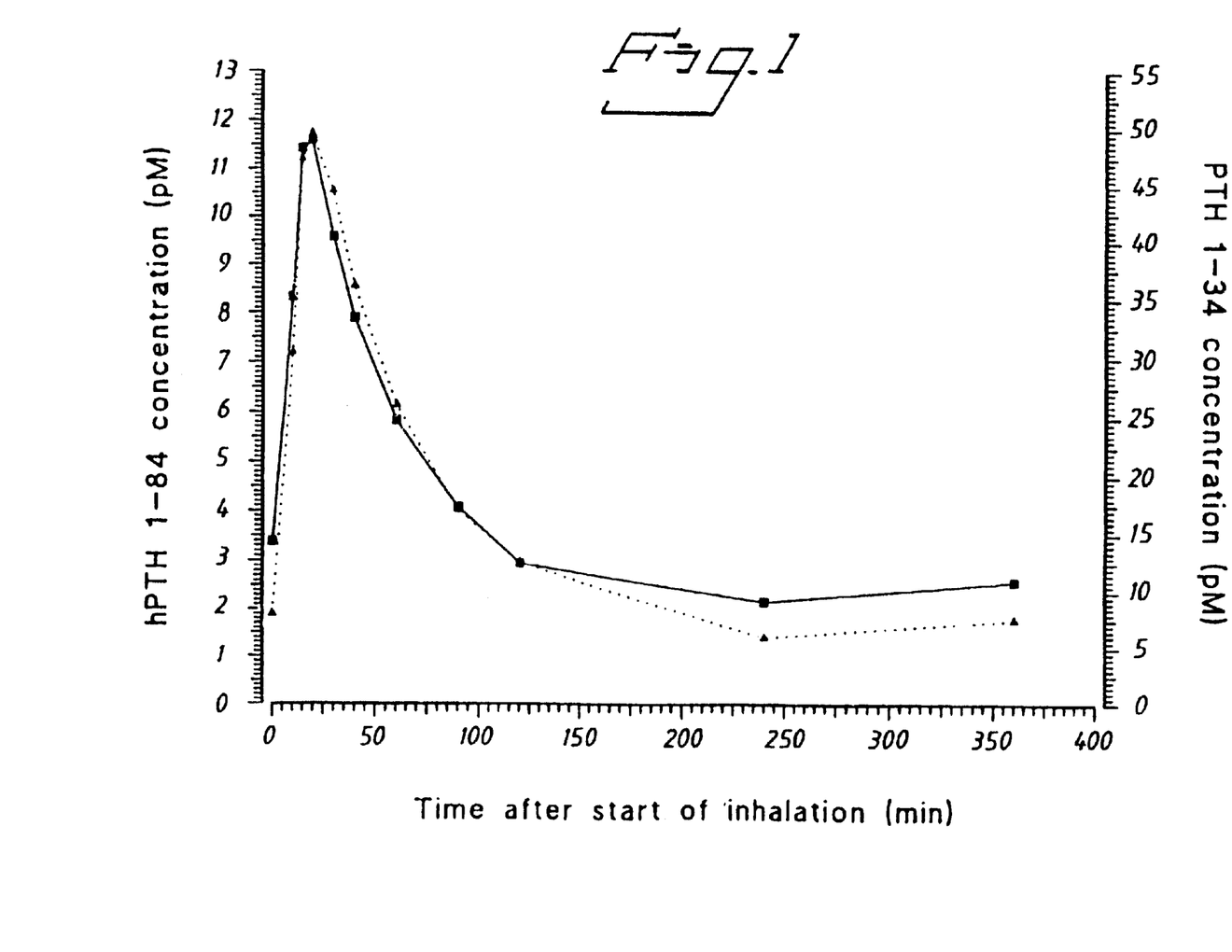

The results (Table 1 and FIG. 1) clearly show that inhalation of both PTH 1–34 and PTH 1–84 results in a pulsatile serum profile similar to that obtained with subcutaneous administration of PTH, confirming that pulmonary administration of full-length ?PTH, or a PTH fragment having substantially the biological activities of full-length PTH, will be effective for stimulating bone formation and for the treatment of osteoporosis.

EXAMPLE 3

Bone effect

The bone effect is measured in ovariectomized osteopenic rats as mineral density as weight/volume of the distal femur after 4 weeks of administration; starting 6 weeks post ovariectomy. The obtained results show that inhalation of full-length PTH has a significant effect on femur bone formation.

TABLE 1

Plasma concentration of PTH in dogs after inhalation of PTH 1–34 or PTH 1–84

| Time (min) | PTH 1–34 | | PTH 1–84 | |
| --- | --- | --- | --- | --- |
| | Conc. (pM) | S.E. | Conc. (pM) | S.E. |
| 0 | 8.0 | 1.82 | 3.4 | 1.02 |
| 10 | 30.4 | 4.99 | 8.3 | 1.04 |
| 15 | 47.4 | 5.20 | 11.4 | 1.01 |
| 20 | 49.6 | 6.81 | 11.6 | 1.11 |
| 30 | 44.6 | 8.55 | 9.6 | 1.15 |
| 40 | 36.2 | 6.84 | 7.9 | 1.21 |
| 60 | 26.0 | 4.90 | 5.8 | 0.84 |
| 90 | 17.0 | 2.05 | 4.1 | 0.60 |
| 120 | 12.6 | 2.06 | 3.0 | 0.36 |
| 240 | 6.0 | 1.76 | 2.2 | 0.40 |
| 360 | 7.6 | 2.93 | 2.6 | 0.85 |

S.E. = standard error of mean

What is claimed is:

1. A dry powder inhaler device containing a preparation consisting of a dry powder comprising (i) a parathyroid hormone (PTH), and (ii) a substance that enhances the absorption of PTH in the lower respiratory tract, wherein at least 50% of (i) and (ii) consists of primary particles having a diameter of up to 10 microns, and wherein the substance is selected from the group consisting of a salt of a fatty acid, a bile salt or derivative thereof, a phospholipid, and a cyclodextrin or derivative thereof.

2. A method of delivering parathyroid hormone to a mammal, the method comprising causing the mammal to inhale the dry powder from the dry powder inhaler device of claim 1.

3. The dry powder inhaler device of claim 1, wherein the dry powder further comprises a pharmaceutically acceptable carrier.

4. The dry powder inhaler device of claim 3, characterized in that said carrier consists essentially of particles having a diameter of up to 10 microns such that at least 50% of said dry powder consists of, said primary particles being optionally agglomerated primary particles having a diameter of up to 10 microns.

5. The dry powder inhaler device of claim 4, in which at least 50% of the dry powder consists of primary particles having a diameter of between 1 and 6 microns, said primary particles being optionally agglomerated.

6. The dry powder inhaler device of claim 3, characterized in that said carrier consists essentially of coarse particles, such that an ordered mixture may be formed between said active compounds and the carrier.

7. The dry powder inhaler device of claim 1, in which at least 50% of the total mass of parathyroid hormone in the dry powder consists of primary particles having a diameter of between 1 and 6 microns.

8. The dry powder inhaler device of claim 1, characterized in that the parathyroid hormone is a human parathyroid hormone which comprises at least amino acids 1 to 34 of SEQ ID NO:1.

9. The dry powder inhaler device of claim 8, characterized in that the parathyroid hormone is a human parathyroid hormone which comprises amino acids 1-84 of SEQ ID NO:1.

10. The dry powder inhaler device of claim 3, characterised in that the carrier is selected from mono-, di-, and polysaccharides, sugar alcohols and polyols.

11. The dry powder inhaler device of claim 3, characterised in that the carrier is lactose.

12. The dry powder inhaler device of claim 3, characterized in that the parathyroid hormone is a human parathyroid hormone which comprises at least amino acids 1 to 34 of SEQ ID NO:1.

13. The dry powder inhaler device of claim 4, characterized in that the parathyroid hormone is a human parathyroid hormone which comprises at least amino acids 1 to 34 of SEQ ID NO:1.

14. The dry powder inhaler device of claim 5, characterized in that the parathyroid hormone is a human parathyroid hormone which comprises at least amino acids 1 to 34 of SEQ ID NO:1.

15. The dry powder inhaler device of claim 6, characterized in that the parathyroid hormone is a human parathyroid hormone which comprises at least amino acids 1 to 34 of SEQ ID NO:1.

16. The dry powder inhaler device of claim 7, characterized in that the parathyroid hormone is a human parathyroid hormone which comprises at least amino acids 1 to 34 of SEQ ID NO:1.

17. The dry powder inhaler device of claim 4, characterized in that the parathyroid hormone is a human parathyroid hormone which comprises at least amino acids 1 to 84 of SEQ ID NO:1.

18. The dry powder inhaler device of claim 5, characterized in that the parathyroid hormone is a human parathyroid hormone which comprises at least amino acids 1 to 84 of SEQ ID NO:1.

19. The dry powder inhaler device of claim 6, characterized in that the parathyroid hormone is a human parathyroid hormone which comprises at least amino acids 1 to 84 of SEQ ID NO:1.

20. The dry powder inhaler device of claim 7, characterized in that the parathyroid hormone is a human parathyroid hormone which comprises at least amino acids 1 to 84 of SEQ ID NO:1.

21. The dry powder inhaler device of claim 1, wherein the substance is a salt of a fatty acid.

22. The dry powder inhaler device of claim 21, wherein the salt of a fatty acid is sodium caprate.

23. The dry powder inhaler device of claim 1, wherein the substance is a bile salt.

24. The dry powder inhaler device of claim 23, wherein the bile salt is sodium taurocholate.

25. The dry powder inhaler device of claim 1, wherein the substance is a phospholipid.

26. The dry powder inhaler device of claim 1, wherein the substance is a cyclodextrin.

27. The dry powder inhaler device of claim 1, the primary particles are agglomerated.

28. A method of delivering parathyroid hormone to a mammal, the method comprising causing the mammal to inhale the dry powder from the dry powder inhaler device of claim 3.

29. A method of delivering parathyroid hormone to a mammal, the method comprising causing the mammal to inhale the dry powder from the dry powder inhaler device of claim 4.

30. A method of delivering parathyroid hormone to a mammal, the method comprising causing the mammal to inhale the dry powder from the dry powder inhaler device of claim 5.

31. A method of delivering parathyroid hormone to a mammal, the method comprising causing the mammal to inhale the dry powder from the dry powder inhaler device of claim 6.

32. A method of delivering parathyroid hormone to a mammal, the method comprising causing the mammal to inhale the dry powder from the dry powder inhaler device of claim 7.

33. A method of delivering parathyroid hormone to a mammal, the method comprising causing the mammal to inhale the dry powder from the dry powder inhaler device of claim 8.

34. A method of delivering parathyroid hormone to a mammal, the method comprising causing the mammal to inhale the dry powder from the dry powder inhaler device of claim 9.

35. A method of delivering parathyroid hormone to a mammal, the method comprising causing the mammal to inhale the dry powder from the dry powder inhaler device of claim 10.

36. A method of delivering parathyroid hormone to a mammal, the method comprising causing the mammal to inhale the dry powder from the dry powder inhaler device of claim 11.

37. A method of delivering parathyroid hormone to a mammal, the method comprising causing the mammal to inhale the dry powder from the dry powder inhaler device of claim 12.

38. A method of delivering parathyroid hormone to a mammal, the method comprising causing the mammal to inhale the dry powder from the dry powder inhaler device of claims 13.

39. A method of delivering parathyroid hormone to a mammal, the method comprising causing the mammal to inhale the dry powder from the dry powder inhaler device of claim 14.

40. A method of delivering parathyroid hormone to a mammal, the method comprising causing the mammal to inhale the dry powder from the dry powder inhaler device of claim 15.

41. A method of delivering parathyroid hormone to a mammal, the method comprising causing the mammal to inhale the dry powder from the dry powder inhaler device of claim 16.

42. A method of delivering parathyroid hormone to a mammal, the method comprising causing the mammal to inhale the dry powder from the dry powder inhaler device of claim 17.

43. A method of delivering parathyroid hormone to a mammal, the method comprising causing the mammal to inhale the dry powder from the dry powder inhaler device of claim 18.

44. A method of delivering parathyroid hormone to a mammal, the method comprising causing the mammal to inhale the dry power from the dry powder inhaler device of claim 19.

45. A method of delivering parathyroid hormone to a mammal, the method comprising causing the mammal to inhale the dry powder from the dry powder inhaler device of claim 20.

46. A method of delivering parathyroid hormone to a mammal, the method comprising causing the mammal to inhale the dry powder from the dry powder inhaler device of claim 21.

47. A method of delivering parathyroid hormone to a mammal, the method comprising causing the mammal to inhale the dry powder from the dry powder inhaler device of claim 22.

48. A method of delivering parathyroid hormone to a mammal, the method comprising causing the mammal to inhale the dry powder from the dry powder inhaler device of claim 23.

49. A method of delivering parathyroid hormone to a mammal, the method comprising causing the mammal to inhale the dry powder from the dry powder inhaler device of claim 24.

50. A method of delivering parathyroid hormone to a mammal, the method comprising causing the mammal to inhale the dry powder from the dry powder inhaler device of claim 25.

51. A method of delivering parathyroid hormone to a mammal, the method comprising causing the mammal to inhale the dry powder from the dry powder inhaler device of claim 26.

52. A method of delivering parathyroid hormone to a mammal, the method comprising causing the mammal to inhale the dry powder from the dry powder inhaler device of claim 27.

53. A dry powder inhaler device containing a preparation consisting of a dry powder comprising (i) a full-length parathyroid hormone (PTH), and (ii) a substance which enhances the absorption of PTH in the lower respiratory tract, wherein at least 50% of (i) and (ii) consists of primary particles having a diameter of up to 10 microns.

54. The dry powder inhaler device of claim 53, wherein the dry powder further comprises a pharmaceutically acceptable carrier.

55. The dry powder inhaler device of claim 54, characterized in that said carrier consists essentially of particles having a diameter of up to 10 microns such that at least 50% of said dry powder consists of primary particles having a diameter of up to 10 microns said primary particles being optionally agglomerated.

56. The dry powder inhaler device of claim 55, in which at least 50% of the dry powder consists essentially of primary particles having a diameter of between 1 and 6 microns said primary particles being optionally agglomerated.

57. The dry powder inhaler device of claim 54, characterized in that said carrier consists essentially of coarse particles, such that an ordered mixture may be formed between said active compounds and the carrier.

58. The dry powder inhaler device of claim 53, in which at least 50% of the total mass of parathyroid hormone in the dry powder consists of primary particles having a diameter of between 1 and 6 microns.

59. The dry powder inhaler device of claim 53, characterized in that the full-length parathyroid hormone is a human full-length parathyroid hormone.

60. The dry powder inhaler device of claim 54, characterised in that the carrier is selected from mono-, di-, and polysaccharides, sugar alcohols, and polyols.

61. The dry powder inhaler device of claim 54, characterised in that the carrier is lactose.

62. The dry powder inhaler device of claim 53, wherein the substance is a salt of a fatty acid.

63. The dry powder inhaler device of claim 62, wherein the salt of a fatty acid is sodium caprate.

64. The dry powder inhaler device of claim 53, wherein the substance is a bile salt.

65. The dry powder inhaler device of claim 64, wherein the bile salt is sodium taurocholate.

66. The dry powder inhaler device of claim 53, wherein the substance is a phospholipid.

67. The dry powder inhaler device of claim 53, wherein the substance is a cyclodextrin.

68. The dry powder inhaler device of claim 53, wherein the primary particles are agglomerated.

* * * * *

UNITED STATES PATENT AND TRADEMARK OFFICE
CERTIFICATE OF CORRECTION

PATENT NO. : 6,436,902 B1
DATED : August 20, 2002
INVENTOR(S) : Kjell G. E. Bäckström et al.

It is certified that error appears in the above-identified patent and that said Letters Patent is hereby corrected as shown below:

<u>Column 7,</u>
Line 42, insert the following:

-- SEQUENCE LISTING

<110>  Bäckström, Kjell G. E.
       Wallmark, Bjorn
       Dahlbäck, Magnus
       Edman, Peter
       Johansson, Ann <120>  THERAPEUTIC PREPARATIONS FOR INHALATION <130>  06275-110002

<140>  US 09/383,590
<141>  1999-08-26

<150>  US 08/586,768
<151>  1996-01-30

<150>  PCT/SE95/01475
<151>  1995-12-08

<150>  SE 9404449-2
<151>  1994-12-22

<150>  SE 9502576-3
<151>  1995-07-12

<160>  1

UNITED STATES PATENT AND TRADEMARK OFFICE
CERTIFICATE OF CORRECTION

PATENT NO.     : 6,436,902 B1
DATED          : August 20, 2002
INVENTOR(S)    : Kjell G. E. Bäckström et al.

It is certified that error appears in the above-identified patent and that said Letters Patent is hereby corrected as shown below:

<u>Column 7 cont'd,</u>
<170> FastSEQ for Windows Version 4.0

<210> 1
<211> 84
<212> PRT
<213> Homo sapiens

<400> 1

```
Ser Val Ser Glu Ile Gln Leu Met His Asn Leu Gly Lys His Leu Asn
 1               5                   10                  15
Ser Met Glu Arg Val Glu Trp Leu Arg Lys Lys Leu Gln Asp Val His
            20                  25                  30
Asn Phe Val Ala Leu Gly Ala Pro Leu Ala Pro Arg Asp Ala Gly Ser
            35                  40                  45
Gln Arg Pro Arg Lys Lys Glu Asp Asn Val Leu Val Glu Ser His Glu
    50                  55                  60
Lys Ser Leu Gly Glu Ala Asp Lys Ala Asp Val Asn Val Leu Thr Lys
65                  70                  75                  80
Ala Lys Ser Gln --
```

Signed and Sealed this

Fifteenth Day of April, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,436,902 B1
DATED : August 20, 2002
INVENTOR(S) : Magnus Dahlbäck et al.

It is certified that error appears in the above-identified patent and that said Letters Patent is hereby corrected as shown below:

Title page,
Item [56], References Cited, OTHER PUBLICATIONS, add
-- Salzman et al., "intranasal Aerosolized…", The New England Journal of Medicine, 312: 1078-1084, 1985. --.

Column 1,
Line 55, delete "(ME84)" and replace with -- (PTH84) --.

Column 4,
Line 21, insert -- . -- after "market".
Line 35, insert -- - -- after "B" and before "0".

Column 5,
Line 18, delete "." after "C".

Column 6,
Line 8, delete "." after "C".
Line 39, delete "." after "C".

Column 7,
Line 9, delete "?" before "PTH".

Signed and Sealed this

First Day of February, 2005

JON W. DUDAS
*Director of the United States Patent and Trademark Office*